(12) United States Patent
Bart et al.

(10) Patent No.: US 12,222,483 B2
(45) Date of Patent: Feb. 11, 2025

(54) READING CODES VIA A SURGICAL MICROSCOPE CAMERA

(71) Applicant: Carl Zeiss Meditec AG, Jena (DE)

(72) Inventors: Florian Bart, Aalen (DE); Axel Lorenz, Meissen (DE); Frank Koenig, Aalen (DE); Frank Keib, Aalen (DE)

(73) Assignee: Carl Zeiss Meditec AG, Jena (DE)

( * ) Notice: Subject to any disclaimer, the term of this patent is extended or adjusted under 35 U.S.C. 154(b) by 707 days.

(21) Appl. No.: 17/212,967

(22) Filed: Mar. 25, 2021

(65) Prior Publication Data

US 2021/0302707 A1    Sep. 30, 2021

(30) Foreign Application Priority Data

Mar. 26, 2020    (DE) .................... 10 2020 108 345.9

(51) Int. Cl.
```
G02B 21/00      (2006.01)
A61B 90/00      (2016.01)
A61B 90/96      (2016.01)
G02B 21/36      (2006.01)
```

(52) U.S. Cl.
CPC ........ *G02B 21/0012* (2013.01); *A61B 90/361* (2016.02); *A61B 90/96* (2016.02); *G02B 21/361* (2013.01)

(58) Field of Classification Search
CPC ....... A61B 90/96; A61B 90/361; A61B 90/90; A61B 90/92; A61B 90/94; A61B 2090/363; A61B 2090/3937; A61B 2090/3945; A61B 2090/395; A61B 2090/3983; A61B 2090/3995; G02B 21/0012; G02B 21/361; G02B 21/008; G02B 21/36; G02B 21/365
See application file for complete search history.

(56) References Cited

U.S. PATENT DOCUMENTS

| 6,167,295 A | 12/2000 | Cosman |
| 6,763,286 B2 | 7/2004 | Metelski |
| 8,675,285 B2 | 3/2014 | Obrebski |
| 11,348,257 B2 * | 5/2022 | Lang ..................... A61B 34/25 |
| 2004/0190129 A1 | 9/2004 | Peter et al. |

(Continued)

FOREIGN PATENT DOCUMENTS

| CA | 2993417 A1 | 3/2017 |
| DE | 10 2009 011 681 A1 | 8/2010 |

(Continued)

OTHER PUBLICATIONS

English translation and Office action of the German Patent Office dated Jan. 12, 2021 in German patent application 10 2020 108 345.9 on which the claim of priority is based.

*Primary Examiner* — Stephone B Allen
*Assistant Examiner* — Adam W Booher
(74) *Attorney, Agent, or Firm* — Walter Ottesen, P.A.

(57) ABSTRACT

A method for operating a surgical microscope having a camera is described. The method includes the following steps: a code that is able to be captured in a set frequency range is introduced into the field of view of the camera, at least one image which includes the code is captured via the camera, an evaluation device is used to identify the code and compare the latter to set features of a code required to activate at least one function, and if the identified code has the set features, the activation of the function is authorized.

11 Claims, 1 Drawing Sheet

(56) References Cited

U.S. PATENT DOCUMENTS

| | | | | |
|---|---|---|---|---|
| 2014/0148818 A1* | 5/2014 | Komuro | ............... | A61B 17/29 |
| | | | | 606/130 |
| 2016/0324593 A1 | 11/2016 | El-Haddad et al. | | |
| 2018/0250085 A1* | 9/2018 | Simi | ................ | A61B 34/71 |
| 2018/0326592 A1 | 11/2018 | Kogan | | |
| 2019/0027247 A1* | 1/2019 | Soto Santos | ........... | G16H 40/67 |
| 2019/0378610 A1* | 12/2019 | Barral | ................ | G09B 19/24 |
| 2020/0409129 A1* | 12/2020 | Themelis | ........... | G02B 21/0012 |

FOREIGN PATENT DOCUMENTS

| | | |
|---|---|---|
| DE | 10 2017 121 483 B3 | 3/2019 |
| EP | 1 193 438 A2 | 4/2002 |

* cited by examiner

READING CODES VIA A SURGICAL MICROSCOPE CAMERA

CROSS REFERENCE TO RELATED APPLICATION

This application claims priority of German patent application no. 10 2020 108 345.9, filed Mar. 26, 2020, the entire content of which is incorporated herein by reference.

FIELD OF THE INVENTION

The disclosure relates to a method for operating a surgical microscope including a camera, in particular having a camera integrated into the surgical microscope. Moreover, the disclosure relates to a surgical microscope and an arrangement for performing a surgery.

BACKGROUND OF THE INVENTION

The amount of electronics and software used in modern surgical microscopes is steadily increasing. Prior to surgery, the users must frequently test various functions in order to check the function of the device and ensure greater patient safety. To this end, it is necessary to activate various menus throughout the test. In this respect, it is necessary to perform various entries on the user interface (GUI-graphical user interface). By way of example, it is necessary to enter codes and passwords, in particular for calling and activating functions, in particular for calling a service mode. Furthermore, certain input sequences must be entered in a set order for the test or the calibration of certain functions, for example, fluorescence options. Under certain circumstances, the release of specific functions or modes of operation requires the input of passwords and/or license keys. By way of example, in some disciplines surgical microscopes are packaged with a sterile drape in order to protect the patient and avoid outlay in relation to cleaning the microscope. The drape pump continuously removes the air between drape and microscope in order to ensure better contact of the drape. By way of example, a password must be entered in order to start the drape pump. It is usually necessary to enter serial numbers in order to use either installed components or components to be additionally used.

As a rule, the manual input of codes, passwords, and serial numbers via a user interface is time-consuming and susceptible to errors. It should be noted that these inputs, as described above, have to be performed multiple times during the assembly of each individual device, and also in the field or in the case of servicing at the customer. In the process, the data to be entered generally have to be read. It is virtually impossible for the technician or the member of servicing staff to know these numbers off by heart since each device is provided with individual codes and passwords. Moreover, time-varying codes or temporary codes may also be provided. As a result, scanning static codes using conventional barcode scanners is no longer a suitable option.

A certain procedure must usually be run through in order to test and/or calibrate certain functions. As a rule, the user must run through a certain input sequence in this case. It is usually not possible to automatically log the performance.

It is possible to use an RFID reader (RFID-radiofrequency identification), which releases a certain function when a corresponding RFID target is held against the reader. That is, the license management is carried out by the RFID reader and the RFID target. This system is complicated and expensive since individual hardware, specifically the RFID reader, must be installed in this case. This significantly increases the production costs of the device. The RFID target on the drape also leads to higher production costs, albeit only to a relatively small increase. Moreover, an RFID reader also means significantly increased complexity within the scope of the approval of the device since the reading method uses radio waves which require a radio license and possibly an EMC test. Furthermore, the read regions must be taken into account when configuring the device, that is, they must be available or appropriately labeled within the scope of industrial design.

Document US 2016/0324593 A1 discloses a surgical microscope with an integrated intraoperative scanner system, via which the position of the tip of an instrument can be tracked. Document U.S. Pat. No. 6,167,295 discloses a camera for carrying out surgery, in particular neurosurgical operations. A surgical microscope for carrying out eye surgery is disclosed in document CA 2 993 417 A1. Here, the surgical microscope includes an optical scanner in the form of a camera for obtaining additional information about certain regions of the eye tissue. The input of information about a reader for the operation of a stand is disclosed in document EP 1 193 438 A2. Here, accessory parts are recognized automatically, for example by way of an automatically readable barcode that is applied to one side of an accessory part and automatically captured by a reader during assembly. Document US 2018/0326592 A1 describes a manipulator system which includes a reader for scanning codes. The operation of the manipulator system is activated on the basis of a corresponding code input.

SUMMARY OF THE INVENTION

It is an object of the invention to provide an advantageous method for operating a surgical microscope, as a result of which, in particular, the use of codes is facilitated in simpler and, at the same time, more reliable fashion.

The aforementioned object can, for example, be achieved via a method for operating a surgical microscope having a camera. The method includes: introducing a code that is able to be captured in a set frequency range into a field of view of the camera; capturing at least one image which includes the code via the camera; identifying the code and comparing the code to set features of an activation code required to activate a function via an evaluation device; and, authorizing an activation of the function if the identified code has the set features.

It is a further object to provide an advantageous surgical microscope. This object can, for example, be achieved via a surgical microscope including: a camera defining a field of view and being configured to capture an image including a code which is in the field of view, wherein the code is detectable in a set frequency range; an evaluation device configured to identify the code and compare the code to set features of an activation code required to activate a function; and, the evaluation device being further configured to authorize an activation of the function if the identified code has the set features.

It is a further object to provide an arrangement for carrying out a surgery. This object can, for example, be achieved via an arrangement for performing a surgery. The arrangement includes: a surgical microscope having a camera and an evaluation device; the camera defining a field of view and being configured to capture an image including a code which is in the field of view, wherein the code is detectable in a set frequency range; the evaluation device being configured to identify the code and compare the code to set features of an activation code required to activate a function; the evaluation device being further configured to authorize an activation of the function if the identified code has the set features; and, at least one accessory component for use within the scope of the surgery, wherein a release of the function of the accessory component requires the input of the code, wherein the code is readable via the camera of the surgical microscope.

The methods according to the disclosure for operating a surgical microscope relate to a surgical microscope including a camera. The method includes the following steps: A code able to be captured in a set frequency range, for example between 400 nanometers and 1,000 nanometers, that is, able to be captured or imaged in the visual or near infrared (NIR) range, is brought into the field of view of a camera. In the process, the code can be guided into the field of view of the camera and/or the field of view of the camera can be directed at the code. At least one image including the code is captured, that is, read or scanned, via the camera. This is preferably implemented in digital fashion. An evaluation device is used to identify the code and compare the latter to set features of a code required to activate at least one function, preferably an operating function. If the identified code has the set features, the activation of the function is authorized. Expressed differently, the function is only operable, that is, activatable and deactivatable and/or controllable, in particular subjectable to closed-loop control, following the authorization.

The camera and/or the evaluation device can be integrated in the surgical microscope or be a constituent part of the surgical microscope, or can be configured as a separate apparatus, for example as a computer connected to the microscope in the case of the evaluation device. The function to be authorized for activation can be, for example, a function of the surgical microscope itself or a function of an accessory device or a component or element to be used in conjunction with the operation of the surgical microscope.

By way of example, the visually perceivable code can be printed on a component or element or device or can be applied in the form of a sticker or can be embodied as a printout on a paper or on a chip or as any other marking, for example also as laser engravings or as codes that are displayed on a cellular phone screen.

The methods according to the disclosure are advantageous in that the readout of codes required to operate the surgical microscope or accessory devices can be input directly via the camera of the surgical microscope. In this way, it is possible to reduce or even eliminate potential errors when reading and manually entering codes and passwords, for example, for calling a service mode. The same applies to reading and entering serial numbers of installed components. Moreover, otherwise possibly required RFID hardware on the device is economized, and hence also the radio license required in individual countries to this end. Furthermore, automatic code generation on a mobile device, for example a cellular telephone or tablet, can be used and a code generated thus can be read directly via the camera of the surgical microscope.

Since a video camera is generally installed in modern surgical microscopes, typically in an image capture unit, the method facilitates an extended and hence particularly efficient use of such a camera for inputs which would otherwise usually be implemented by way of a user interface. The method consequently increases the digitization of the surgical microscope and reduces input errors.

In an embodiment, the activation of the function is disabled if the identified code does not have the set features. Thus, the function cannot be actuated in this case. In a further advantageous variant, the at least one function that requires the input of the code is activated, for example started, within the scope of the method according to the disclosure. In this way, one or more functions or entire workflows can be quickly and reliably started by simply scanning a code via the microscope camera. Moreover, the performance of at least the activated function can be logged. The log can preferably be stored. Optionally, further functions, in particular whole workflows, can also be logged and stored where necessary.

By way of example, the function to be activated can be an operating function of the surgical microscope, for example a test function such as, in particular, a white balance, a color balance, a fluorescence function or any other function or a function of a further device, for example a device or component, for example an accessory component, to be used in conjunction with the operation of the surgical microscope.

The camera can be configured as a video camera or an industrial photographic camera with a regular or irregular repetition rate. To this end, the camera and/or the evaluation device can be configured to recognize and identify a code in a captured image, for example in a moving image. Here, the camera and/or the evaluation device can be configured to recognize and identify a code in a captured image, for example, a moving image, via a device for text recognition and/or for pattern recognition. By way of example, the device for text recognition and/or for pattern recognition can be software configured to this end.

By way of example, it is possible to capture a code which is displayed in static or time-varying fashion on an accessory component and/or a mobile device, for example a cellular telephone or tablet, or a display. By way of example, the code can be generated on the mobile device and displayed on a display of the mobile device. In addition or as an alternative thereto, the code can be attached to a component, for example in the form of a sticker or a stamp. Furthermore, the code can be visibly imaged on a chip or a card or a sheet of paper.

By way of example, the code can be configured as a QR code (QR-quick response) and/or data matrix code and/or barcode, for example in the form of a code 39 or in any other form, and/or as a serial number and/or a password.

In a further variant, the camera can include a user interface, via which the captured and/or identified code is displayed. This is advantageous, in particular, in that the user can recognize whether the code was correctly and completely placed within the field of view of the camera.

By way of example, 1-chip cameras, 3-chip cameras, HD cameras, 4k cameras and various further options come into question as camera options and variants. It is possible to use cameras with any sensor size and resolution in 1-chip or 3-chip arrangement, with the minimum requirements being determined by the characteristics of the code. Within the scope of the method according to the disclosure, data to be entered, for example patient data, can also be read and identified as code via the camera. Furthermore, license management, for example the entry of license keys, can also be implemented within the scope of the method according to the disclosure.

The surgical microscope includes a camera and an evaluation device and is configured to carry out an above-described method. The surgical microscope has the features and advantages already specified above in conjunction with the method. In particular, the surgical microscope can include a device for text recognition and/or for pattern recognition.

An arrangement according to the disclosure for performing a surgery includes a surgical microscope according to the disclosure and at least one accessory component for use within the scope of the surgery. Here, releasing at least one function of the accessory component requires input of at least one code, wherein at least this one code is able to be read via the camera of the surgical microscope. By way of example, the accessory component can be a pump, for example a device to be operated automatically within the scope of a surgery, for example an imaging apparatus.

The video image is very important to the surgeon; therefore, a white balance should be started prior to the surgery. A target with a QR code can start this automatically and thus save the surgery staff's time. By processing the code, it is also possible to automatically log that this white balance was in fact also carried out. The same applies to fluorescence targets, which are required for the IR 800, Blue 400 and Yellow 560 functions. Newly installed accessories can thus also be recognized and the correct settings for the accessory can be placed following questioning; this is in addition to simplification for the service technician when these are used during the calibration of special equipment. Some functions of the device are only authorized once as per the requirements in respect of the producer. This authorization can likewise be implemented by way of a sent QR code.

The arrangement for performing a surgery likewise has the aforementioned advantages. In particular, the input of data of a very different type, for example patient data, license data, serial numbers of accessory components, et cetera, can be entered or scanned in quick and reliable fashion. As a result, numerous methods to be carried out in conjunction with a surgery and in conjunction with the servicing of very different elements can be carried out faster and efficiently, and errors can be reduced.

Overall, embodiments according to the present disclosure have the following effects and advantages: They facilitate convenient input of codes and passwords, for example for calling a service mode. By scanning codes on accessories, it is possible to conveniently start functions, for example a white balance or the test of fluorescences, for example, IR 800, Blue 400, Yellow 560. This can then be documented automatically in the device, too, for example as a log file. In particular, a complete workflow can easily be started by the microscope camera via the code input. Furthermore, automatic logging is possible. Moreover, certain functions and/or test licenses can easily be activated by scanning codes. As a result, such an activation becomes simpler for a customer or user and can be implemented digitally. Serial numbers of installed devices and/or accessories can easily be captured via the microscope camera, and, for example, stored in the device. Since codes, for example QR codes, can also be scanned from displays via the camera, it is also possible to scan codes which, for example, were generated by a specific application from a cellular telephone. Thus, it is also possible to use time-varying and/or time-limited codes.

The expression "and/or" used here, when it is used in a series of two or more elements, means that any of the elements listed can be used alone, or any combination of two or more of the elements listed can be used. For example, if a structure is described as containing the components A, B and/or C, the structure can contain A alone; B alone; C alone; A and B in combination; A and C in combination; B and C in combination; or A, B, and C in combination.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
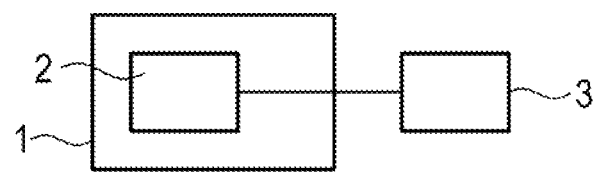
FIG. 1 schematically shows a surgical microscope.

FIG. 1 schematically shows a surgical microscope 1. The surgical microscope 1 includes a camera 2. The surgical microscope 1 is configured to be operated in accordance with an embodiment described in exemplary fashion below on the basis of FIG. 2. To this end, the camera 2 is connected to an evaluation device 3 for data transmission purposes. The evaluation device 3 can be a constituent part of the surgical microscope or can be configured as a separate apparatus, for example, as a computer connected to the surgical microscope.

Figure 2:
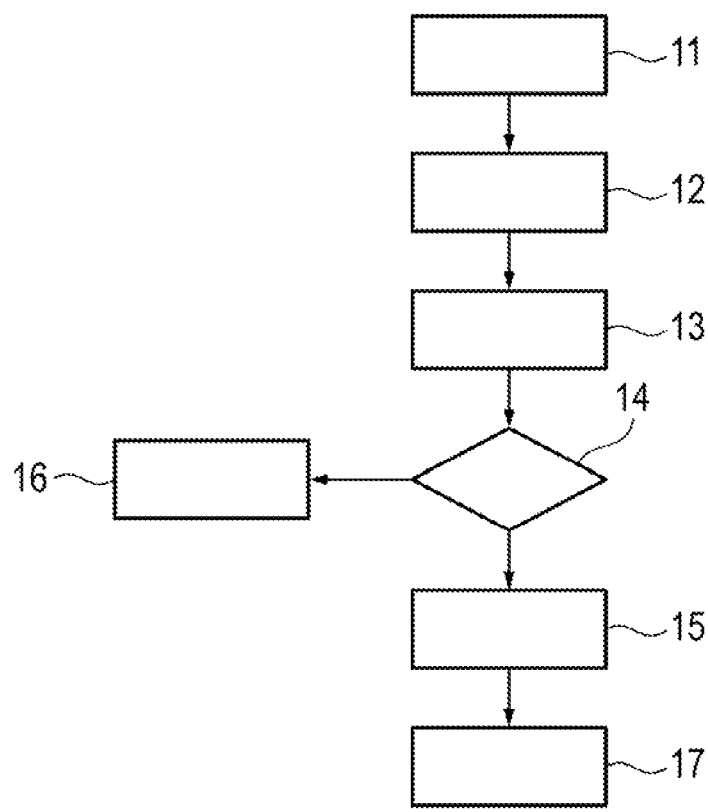
FIG. 2 schematically shows an example for a method according to the disclosure in the form of a flowchart; and, FIG. 3 schematically shows an arrangement according to the disclosure for performing a surgery.

FIG. 2 schematically shows an example for a method according to the disclosure in the form of a flowchart. In a first step 11, a code that is able to be captured in a set frequency range, for example a visually perceivable or imaged code, is introduced into the field of view of the camera 2. To this end, the code can be guided into the field of view of the camera and/or the field of view of the camera can be directed at the code. By way of example, a chip card with a code imaged thereon, for example a barcode or QR code, or a license key printed thereon or a serial number can be guided into the field of view of the camera. By way of example, however, it is also possible to direct the field of view of the camera at a code arranged on an accessory component or at a position in space that is distant from the camera, for example at a license key attached to an accessory component or a serial number or a barcode or a QR code.

At least one image which includes the code is captured via the camera in a second step 12. This is preferably implemented in digital fashion. Expressed differently, the code in the form of an image or an image representation is read or scanned via the camera.

The code is identified via the evaluation device 3 in a third step 13. Furthermore, the evaluation device is used in step 14 to compare the identified code with set features of a code required to activate at least one function. The function to be activated can be a function of the surgical microscope, for example a white balance or any other color balance. However, this can also be a function of an accessory device or a component to be used in conjunction with the operation of the surgical microscope.

If the identified code has the set features, the activation of the function is authorized in a further step 15. If the identified code does not have the set features, that is, for example does not correspond to a set code, the activation of the function is disabled in step 16. The scope of the method according to the disclosure can include an optional step 17, in which the at least one function that requires the input of the code can be activated following step 15 in step 17. Optionally, the surgical microscope, in particular the camera, can include a user interface, via which the captured and/or identified code can be displayed.

The evaluation device 3 and/or the surgical microscope 1, in particular the camera 2, can include a device for text recognition and/or for pattern recognition. A device for text recognition and/or for pattern recognition facilitates the readout and identification of codes with very different configurations, for example, QR codes and/or data matrix codes and/or barcodes and/or serial numbers and/or passwords.

Figure 3:
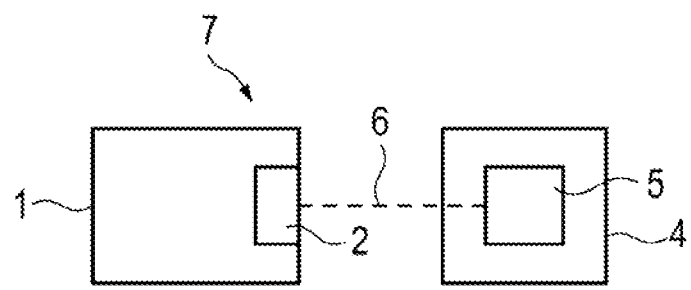

FIG. 3 schematically shows an arrangement 7 according to the disclosure for performing a surgery. The arrangement 7 includes a surgical microscope 1 according to the disclosure with a camera 2 and an accessory component 4, on which a code 5 has been attached in the example shown. The code 5 is able to be read via the camera 2. This is indicated by a dashed line 6.

Various specific application examples are described below. The first example relates to the option of entering a password. Recognition by way of reading the code via a camera, configured as a video camera, of the surgical microscope can be offered as an option, for example at the user interface of the device, that is, for example the surgical microscope and/or the camera. To this end, a button, for example, can be provided next to an input field. By way of example, such a button may appear when the password for a function, for example the service mode, is queried. When this button is clicked, the video system of the device is put into a mode in which codes are searched for and identified in the video image. As soon as a code was recognized, the corresponding value, for example the password in the present case, is automatically entered into the form. Hence, the manual input is dispensed with.

A further option consists of reading the code from a display. In this case, the code for the service mode, for example, can also be generated on a cellular telephone or any other mobile device and can be read directly from the display of the mobile device, for example the cellular telephone. Consequently, the password can be entered very quickly, conveniently and, at the same time, in a fail-safe manner. Changing or time-dependent codes can also be generated by a cellular phone or tablet in this case. That is, static codes are no longer required, significantly increasing the security. A code/password that falls into the wrong hands therefore quickly expires and can no longer be used.

A second application example relates to the input of serial numbers. Serial numbers of additional components are usually manually entered on the device computer. Within the scope of the present disclosure, the serial number, which can be attached on the component itself, for example as a label, can easily be captured by scanning via the camera of the surgical microscope and can be stored accordingly. This reduces the outlay during the assembly. Since a second label is usually also supplied with components requiring a serial number, the second label can be stuck into a product file, for example, and can be scanned via the camera when necessary. A corresponding procedure can also be applied for servicing, for example if components are replaced in the field or at the customer and the new serial numbers then need to be entered into a computer.

A third application example relates to ordering of replacement parts in the case of a remote service. Should a device in the field or at the customer be defective, the label with the code of the faulty component can be scanned, to be precise directly via the microscope camera. Then, the device can be linked via a remote service to the server of the producer and can display the corresponding replacement part kit, can display further instructions or optionally can even facilitate ordering of the replacement part. This facilitates a very quick and simpler repair. In particular, searching a database, selecting material numbers, et cetera, are dispensed with.

A fourth application example relates to the license management of an auto drape function. Instead of holding an RFID target of a drape against the RFID reader additionally installed to this end, as has been customary up until now, a corresponding code, for example a data matrix code, can simply be applied to the drape within the scope of the present disclosure. The data matrix code can then be read optically via the camera of the surgical microscope instead of via RFID technology. If a valid data matrix code is used, the auto drape function is authorized and activated where necessary. An advantage over the conventional RFID solution consists in the production costs for the device and the drape being reduced since, firstly, there is no need for an RFID reader and no need for an RFID target on the drape and, moreover, there is no need for a radio license for the individual countries. Naturally, other functions can also be controlled as described, in a manner analogous to an auto drape function.

A further application example relates to the reading of QR codes on accessories. Reading of QR codes attached to accessory components is implementable in a significantly simpler manner via the present disclosure. By way of example, a function of the device can be activated very easily via an accessory component. In particular, an IR 800 mode can be tested automatically, and the check can be documented when a certain code on a target is captured and identified. Furthermore, a Blue 400 mode can be tested automatically, and the check can be documented when a certain code on a target is captured and identified. Analogously, a Yellow 560 mode can be tested automatically, and the check can be documented when a certain code on a target is captured and identified. A white balance for the video camera can be started by way of a QR code of a target. Likewise, service functions can be started during an assembly or adjustment if the respective QR code is recognized. An activation application can also be released directly via a software license key via a cellular phone or via any other mobile device by virtue of a corresponding code displayed on the mobile device on a display being read via the microscope camera.

The aforementioned tests being performed can also be logged directly in the respective system, that is, for example, via the evaluation device. This ensures that certain device functions, for example fluorescence, are ensured. By way of example, in conjunction with surgery this increases the patient safety. Overall, the present disclosure allows time to be saved in conjunction with the assembly, the construction and the operation of a surgical microscope. The procedure becomes more effective and quicker for a user. This increases convenience and achieves a higher level of digitalization.

It is understood that the foregoing description is that of the preferred embodiments of the invention and that various changes and modifications may be made thereto without departing from the spirit and scope of the invention as defined in the appended claims.

LIST OF REFERENCE SIGNS

1 Surgical microscope
2 Camera
3 Evaluation device
4 Accessory component
5 Code
6 Capturing the code via the camera
7 Arrangement for performing a surgery
11 Bringing the code into a field of view of the camera
12 Capturing the code
13 Identifying the code
14 Comparing the identified code to set features of a code required for activating at least one function 15 Authorizing the activation of the function if the identified code has the set features
16 Disabling the activation of the function if the identified code does not have the set features
17 Activate function

What is claimed is:

1. A method for operating a surgical microscope having a camera and an evaluation device as integral components of the surgical microscope, the camera being connected to the evaluation device to facilitate data transmission therebetween, the method comprising:
introducing a code that is able to be captured in a set frequency range of 400 to 1000 nanometers directly into a field of view of the camera;
capturing at least one image which includes the code via the camera by scanning the image which includes the code;
identifying the code via the evaluation device;
comparing the identified code via the evaluation device to set features of an activation code required to activate an operating function of the surgical microscope;
thereafter, one of the following applies:
i) if the comparison shows that the identified code has the set features of the activation code, an activation of the operating function of the surgical microscope is authorized via the evaluation device; or,
ii) if the comparison shows that the identified code does not have the set features of the activation code, the activation of the operating function of the surgical microscope is disabled;
activating the operating function associated with the activation code in response to authorization thereof; and,
wherein the camera for facilitating said data transmission includes a device for text recognition and pattern recognition to facilitate reading out and identifying codes of different configuration including QR codes and/or data matrix codes and/or barcodes and/or serial numbers and passwords.

2. The method of claim 1 further comprising logging a performance of the activated function.

3. The method of claim 1, wherein the camera is a video camera or an industrial photographic camera with a regular or irregular repetition rate.

4. The method of claim 1, wherein at least one of the camera and the evaluation device are configured to recognize and identify the code in a captured image.

5. The method of claim 4, wherein at least one of the camera and the evaluation device are configured to recognize and identify the code in the captured image via a device for at least one of text recognition and pattern recognition.

6. The method of claim 1, wherein the code is displayed in at least one of a static and time-varying manner on at least one of an accessory component, a mobile device, and a display.

7. The method of claim 6, wherein the code is at least one of attached to a component, visible on a chip, and visible on a card.

8. The method of claim 1, wherein the code is at least one of attached to a component, visible on a chip, and visible on a card.

9. The method of claim 1, wherein the code is configured as at least one of a QR code, data matrix code, barcode, serial number, and password.

10. The method of claim 1, wherein the camera includes a user interface via which at least one of the code included in the captured image and the identified code is indicated.

11. A surgical microscope comprising:
a camera defining a field of view and being configured to capture an image including a code which is in said field of view, wherein the code is detectable in a set frequency range;
an evaluation device connected to said camera to permit data transmission therebetween;
said evaluation device being configured to identify the code and compare the identified code to set features of an activation code required to activate a function of the surgical microscope; and,
said evaluation device being further configured to authorize an activation of the function of the surgical microscope if the identified code has the set features; and,
wherein the camera facilitates said data transmission and includes a device for text recognition and pattern recognition to permit reading out and identifying codes of different configuration including QR codes and/or data matrix codes and/or barcodes and/or serial numbers and passwords.

* * * * *